US011134904B2

United States Patent
Lauritsch et al.

(10) Patent No.: US 11,134,904 B2
(45) Date of Patent: Oct. 5, 2021

(54) SCATTERED RADIATION COMPENSATION FOR A MEDICAL IMAGING APPLIANCE

(71) Applicants: Günter Lauritsch, Nuremberg (DE); Michael Manhart, Fürth (DE); Sebastian Bauer, Erlangen (DE)

(72) Inventors: Günter Lauritsch, Nuremberg (DE); Michael Manhart, Fürth (DE); Sebastian Bauer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 455 days.

(21) Appl. No.: 15/803,380

(22) Filed: Nov. 3, 2017

(65) Prior Publication Data

US 2018/0125438 A1    May 10, 2018

(30) Foreign Application Priority Data

Nov. 4, 2016    (DE) .......................... 102016221658.9

(51) Int. Cl.
*A61B 6/00* (2006.01)
*A61B 6/06* (2006.01)
(Continued)

(52) U.S. Cl.
CPC ............. *A61B 6/4014* (2013.01); *A61B 6/06* (2013.01); *A61B 6/4291* (2013.01);
(Continued)

(58) Field of Classification Search
None
See application file for complete search history.

(56) References Cited

U.S. PATENT DOCUMENTS 4,123,654 A * 10/1978 Reiss ..................... A61B 6/032
378/5
7,396,162 B1 * 7/2008 Edie ..................... A61B 6/5282
378/207
(Continued)

FOREIGN PATENT DOCUMENTS

CN    101028195 A    9/2007
CN    101061957 A    10/2007
(Continued)

OTHER PUBLICATIONS

Rührnschopf, Ernst-Peter et al., "A general framework and review of scatter correction methods in cone beam CT. Part 2: Scatter estimation approaches," Med. Phys. 38 (9), Sep. 2011, p. 5186-5199; 2011.
(Continued)

*Primary Examiner* — Edwin C Gunberg
(74) *Attorney, Agent, or Firm* — Lempia Summerfield Katz LLC

(57) ABSTRACT

A method for operating a medical imaging apparatus includes acquiring an intensity distribution of an X-ray radiation by a first X-ray detector assigned to a first radiation source. A scattered radiation distribution of scattered radiation generated at the object is acquired by a second X-ray detector. A spatial distribution for the component of the scattered radiation is estimated based on the scattered radiation distribution acquired by the second X-ray detector. An intensity distribution of the component of the transmitted primary X-ray radiation is determined from the intensity distribution acquired by the first X-ray detector depending on the estimated spatial distribution.

17 Claims, 1 Drawing Sheet

(51) Int. Cl.
*G01T 1/16* (2006.01)
*G01T 1/29* (2006.01)
*A61B 6/03* (2006.01)

(52) U.S. Cl.
CPC ............ *A61B 6/4441* (2013.01); *A61B 6/483* (2013.01); *A61B 6/5205* (2013.01); *A61B 6/5282* (2013.01); *A61B 6/584* (2013.01); *G01T 1/1603* (2013.01); *G01T 1/2914* (2013.01); *A61B 6/03* (2013.01); *A61B 6/032* (2013.01)

(56) References Cited

U.S. PATENT DOCUMENTS

| | | | |
|---|---|---|---|
| 2003/0128801 A1* | 7/2003 | Eisenberg | A61B 6/032 378/19 |
| 2004/0079232 A1 | 4/2004 | Groh et al. | |
| 2007/0086561 A1 | 4/2007 | Bruder | |
| 2007/0253524 A1 | 11/2007 | Bruder | |
| 2007/0253525 A1 | 11/2007 | Popescu | |
| 2009/0147911 A1 | 6/2009 | Joosten | |
| 2011/0311019 A1 | 12/2011 | Ribbing | |
| 2013/0004050 A1 | 1/2013 | Wu | |
| 2013/0248719 A1 | 9/2013 | Volokh | |
| 2018/0284035 A1 | 10/2018 | Steadman Booker | |

FOREIGN PATENT DOCUMENTS

| | | | |
|---|---|---|---|
| CN | 101061958 A | 10/2007 | |
| CN | 101065685 A | 10/2007 | |
| CN | 101472525 A | 7/2009 | |
| CN | 101987021 A | 3/2011 | |
| CN | 102846333 A | 1/2013 | |
| CN | 103315760 A | 9/2013 | |
| CN | 104161536 A | 11/2014 | |
| DE | 10232429 B3 | 1/2004 | |
| WO | 2017071952 A1 | 5/2017 | |

OTHER PUBLICATIONS

Rührnschopf, Ernst-Peter et al., "A general framework and review of scatter correction methods in x-ray cone-beam computerized tomography. Part 1: Scatter compensation approaches," Med. Phys. 38 (7), Jul. 2011, pp. 4296-4311; 2011.

Siewerdsen, J.H. et al. "A simple, direct method for x-ray scatter estimation and correction in digital radiography and cone-beam CT," Med. Phys. 33 (1), pp. 187-197; 2006.

Barrett, H. et al; "Radiological Imaging: The Theory of Image Formation, Detection, and Processing"; Appendix C ("Interaction of Photons with Matter"), Academic Press, pp. 315-334; 1981.

German Office Action for related German Application No. 10 2016 221 658.9 dated Apr. 20, 2017.

Siewerdsen, Jeffrey H. et. al.; "Cone-beam computed tomography with a flat-panel imager: Magnitude and effects of x-ray scatter"; in Medical Physics; vol. 28, No. 2, pp. 220-231; Feb. 2001.

Chinese Office Action for Chinese Application No. 201711069236.0 dated Aug. 31, 2020, with English translation.

* cited by examiner

SCATTERED RADIATION COMPENSATION FOR A MEDICAL IMAGING APPLIANCE

This application claims the benefit of DE 10 2016 221 658.9, filed on Nov. 4, 2016, which is hereby incorporated by reference in its entirety.

BACKGROUND

The present embodiments relate to operating a medical imaging apparatus.

In X-ray imaging, scattered radiation has a fundamental influence on image quality. The scattered radiation is created during the irradiation of an object in the context of producing an X-ray recording of the object as a result of the fact that primary X-ray radiation traveling out from a radiation source and, for example, restricted by a collimator in the sense of spatial limitation, is not only partly absorbed in an object but also scattered. This is comprehensively explained, for example, in Biological Imaging: The theory of image formation, detection and processing—Volume 1, Academic Press, 1996, by H. Barrett and W. Swindell. In the field of medical imaging (e.g., X-ray diagnostics), two interactions with an object (e.g., an organ of a patient) that result in the formation of scattered rays occur. This is the classical elastic Rayleigh scattering and the non-elastic Compton scattering. In principle, any scattered radiation results (e.g., due to a lowering of contrast and an intensification of image noise) in a lessening of the quality of the X-ray recording and therefore also of an image reconstructed from the X-ray recording. The introduction of large-area X-ray detectors and the associated enlargement of corresponding cone beam aperture angles for the primary radiation, which may be adjusted by the corresponding collimator, in radiography, C-arm imaging, and also in computed tomography, has resulted in a distinct intensification of the scattered ray problem. This is due to the component of the scattered radiation markedly increasing with increasing size of the irradiated object (e.g., a pelvis) and also with the size of a detector spatial angle (e.g., of the spatial angle from which the X-ray detector detects X-ray radiation).

The lowering of contrast alluded to plays a major role precisely in the case of 3D imaging (e.g., the reconstruction of a three-dimensional image of the irradiated object), such as occurs, for example, in computed tomography or in C-arm computed tomography. In the case of 3D imaging, one projection image is recorded in each case from different directions (e.g., projection directions), and a 3D image dataset is obtained and a 3D image reconstructed from the projection image. In addition to the lowering of contrast, scattered radiation causes further artifacts such as, for example, stronger noise, strong low-frequency gray level deformation, cupping or capping, and also line or respectively shadow artifacts in the reconstructed three-dimensional image, for example. The article "Cone-beam computed tomography with a flat-panel imager: Magnitude and effects of x-ray scatter" in Medical Physics 28 (2) pp. 220 to 231 from the year 2001 by J. Siewerdsen and D. Jaffray provides a comprehensive investigation of scattered radiation and corresponding affects on image quality in C-arm CT systems.

Accordingly, a reduction in scattered radiation or a correction or compensation of a corresponding influence of scattered radiation on a 2D or 3D image is desirable in the field of medical imaging. A distinction is made between hardware-based and software-based approaches.

Hardware-based approaches include, for example, scattered ray grids that are fitted in front of the X-ray detector (e.g., in front of the detector cells of the X-ray detector). The walls of the scattered ray grid are aligned with an assigned radiation source. Increasing the distance between the irradiated object and the X-ray detector, where this is practicable, may also contribute to reducing the scattered radiation. Hardware-based approaches are aimed at physically suppressing scattered radiation before the scattered radiation impinges on the X-ray detector.

Software-based approaches are typically devoted to reducing the residual scattered radiation (e.g., reducing the component of the scattered radiation that is not eliminated by hardware-based methods). This residual or remnant scattered radiation component that is acquired by the X-ray detector may in some cases still be larger in a signal generated by the X-ray detector than the transmitted component of the primary radiation (e.g., larger than the primary radiation component). Software-based approaches are accordingly aimed at post-processing of the X-ray radiation or distribution as acquired by the X-ray detector, which includes or is formed by both the primary radiation component and also the scattered radiation.

Software-based approaches may include two components in this regard: a method for estimating a spatial distribution of the scattered radiation on the X-ray detector and therefore in a measured projection image; and a correction or respectively compensation algorithm that in the simplest case subtracts the estimated scattered ray distribution from the measured X-ray radiation distribution on the X-ray detector or the measured projection data on the other.

An overview of methods for measuring or estimating and correcting or compensating for scattered radiation is given in the articles "A general framework and review of scatter correction methods in x-ray cone-beam computerized tomography, Part 1: Scatter compensation approaches" in Medical Physics 38 (7), pp. 4296 to 4311 from 2011 and "A general framework and review of scatter correction methods in cone-beam computerized tomography, Part 2: Scatter estimation approaches" in Medical Physics 38 (9), pp. 5186 to 5199 from 2011 by the authors E.-Peter Rührnschopf and K. Klingenbeck. Only relatively few methods are based on an actual measurement of the scattered radiation. Instead, the majority of the approaches adopt the line of estimating the scattered radiation by using mathematical models. This is due to the fact that measuring scattered radiation is costly and may impair acquisition of the X-ray radiation by the X-ray detector and therefore the actual image recording.

For the purpose of measuring scattered radiation, there are approaches that insert additional hardware or an additional object between the radiation source or X-ray source and the irradiated object or measurement object. For example, the additional object may take the form of a ray absorption grid and/or a modulation grid and/or the like. In this regard, the corresponding approaches have the disadvantage that the approaches make additional recordings necessary and therefore raise a corresponding radiation dose for a patient. The approaches have artifacts in the acquired X-ray radiation and therefore in the acquired two-dimensional or respectively reconstructed three-dimensional images. The approaches also demand an extra mechanical effort for practical realization, specifically the insertion and removal of the corresponding reference objects.

There are approaches that utilize a collimator integrated into the medical apparatus. A predetermined region of the X-ray detector is shielded from the primary radiation by the collimator in order to be able to measure the scattered radiation at that point (e.g., in the shadow of the collimator) and estimate the scattered radiation for the rest of the X-ray detector. The estimation or the assessment of the scattered radiation distribution in the field of view (e.g., in the region of the X-ray detector not shielded by the collimator) is then effected, for example, on a model assessment based on the image data created in the collimator shadow as measured at an edge of the X-ray detector. This is described, for example, in the article "A simple, direct method for x-ray scatter estimation and correction in digital radiography and cone-beam computerized tomography" in Medical Physics 33 (1), pp. 187 to 197 from 2006 by J. Siewerdsen et al.

A disadvantage in this respect is that multiple detector rows or detector columns at the detector edge are taken up by the scattered ray measurement, which reduces the maximum possible field of view in terms of size. Additionally, it is questionable how robust a model-based assessment of the scattered ray distribution in the field of view (e.g., in the region of the X-ray detector that acquires the primary beam component of the X-ray radiation) may be if only a few detector rows or detector columns (e.g., a minute region in comparison with the size of the region of scattered radiation to be assessed) are available as a database for the assessment.

SUMMARY AND DESCRIPTION

The scope of the present invention is defined solely by the appended claims and is not affected to any degree by the statements within this summary.

The present embodiments may obviate one or more of the drawbacks or limitations in the related art. For example, quality of an image or image data generated by a medical imaging apparatus is improved. As another example, an improved scattered radiation compensation for a medical imaging apparatus is provided.

In one embodiment, a method for operating a medical imaging apparatus such as, for example, an X-ray apparatus or a computed tomography apparatus with a series of method acts is provided. The apparatus may, for example, take the form of a C-arm apparatus. A first method act is a generation of a primary X-ray radiation by a first radiation source of the medical apparatus. The primary X-ray radiation may be spatially restricted or limited by a collimator according to the principle of a perforated screen and therefore be adapted in terms of spatial extent to a size of a first X-ray detector assigned to the first radiation source. A further method act is the irradiation of an object (e.g., a patient and/or a part of a patient's body) with the primary X-ray radiation. A following method act is a first acquisition of a first intensity distribution of an X-ray radiation by the first X-ray detector of the medical apparatus. The first X-ray detector is assigned to the first radiation source. The first X-ray detector may have a matrix of detector cells that are arranged in multiple rows and multiple lines. The acquired X-ray radiation includes a component of the primary X-ray radiation. The component is transmitted through the object (e.g., not absorbed by the object) and also a component of a scattered radiation generated by a scattering of the primary X-ray radiation at the object. The component is therefore defined, for example, by a primary radiation component and a scattered radiation component. Overall, therefore, the scattered radiation and the transmitted component of the primary X-ray radiation are acquired by the first X-ray detector.

As a further method act, a second acquisition of a scattered radiation distribution of the scattered radiation generated at the object is performed as a second intensity distribution by a second X-ray detector of the medical apparatus. The collimator makes it possible to achieve the outcome that only scattered radiation and no component of the primary X-ray radiation from the first radiation source may be acquired on the second X-ray detector. The second X-ray detector may likewise have a matrix of detector cells that are arranged in multiple rows and multiple columns. Therefore, a component of the primary X-ray radiation and a component of the scattered radiation are acquired by the first X-ray detector, but only a component of the scattered radiation is acquired by the second detector. The acquisition of the scattered radiation distribution by the second X-ray detector includes, for example, an acquisition of a spatial distribution of the scattered radiation on the second X-ray detector. The second X-ray detector may be placed in multiple different locations at a predetermined location (e.g., a predetermined position and/or a predetermined orientation) of the first X-ray detector. The first acquisition and the second acquisition need not be effected consecutively but may also be effected simultaneously.

This is followed as a method act by an estimation of a spatial distribution for the component of the scattered radiation acquired by the first X-ray detector based on the radiation distribution acquired by the second X-ray detector by a computer of the medical apparatus. This may be estimated, for example, by using a suitable mathematical model (e.g., a quadratic model or a polygon curve; a spline). The geometrical location of the two X-ray detectors with respect to each other may also be taken into account in the mathematical model (e.g., relative position and/or relative orientation with respect to each other).

A further method act is then a determination of a second intensity distribution of the component of the transmitted primary X-ray radiation acquired by the first X-ray detector from the first intensity distribution acquired overall by the first X-ray detector depending on the spatial distribution estimated for the scattered radiation on the first X-ray detector by the computer. This may be effected, for example, by using compensation of the scattered radiation in the first intensity distribution acquired overall (e.g., by the familiar subtraction of the estimated or assumed scattered radiation distribution from the first intensity distribution acquired overall or by other known measures). The relative spatial position and orientation of the two X-ray detectors with respect to each other is predetermined and known. For example, a reprocessing of a 2D image of the object, which may also be referred to as reconstruction of a 2D image in the context of this specification, or reconstruction of a 3D image of the object based on the determined second intensity distribution of the transmitted primary X-ray radiation, may also be effected here. In the case of a 2D image the first intensity distribution of the X-ray radiation acquired overall may already correspond to a 2D recording, which may then be subjected to scattered radiation compensation in the context of the reconstruction.

The method described therefore presents an approach to scattered radiation correction that is based on an actual measurement of the scattered radiation with a second X-ray detector that is different from the first X-ray detector. The method is therefore directed primarily toward C-arm systems with two image planes (e.g., biplane systems) with two detector planes, for example. The second X-ray detector that is already present in a biplane system, for example, is utilized for measuring the scattered radiation distribution. Based on this measured scattered radiation distribution, a scattered radiation compensation that is improved compared with conventional methods may be effected for the first intensity distribution acquired by the first X-ray detector. In this regard, the method may be utilized both in 2D and also in 3D imaging. The entire detector region of the first X-ray detector (e.g., all the detector cells of the first X-ray detector) may be utilized for generating the 2D or 3D image. Additionally, the large-area measurement of the scattered radiation in the second X-ray detector (e.g., in the entire detector region of the second X-ray detector) allows a more robust and more precise assessment of the scattered radiation distribution on the first X-ray detector (e.g., of the spatial distribution for the scattered radiation acquired by the first X-ray detector).

An embodiment provides for a matrix of detector cells of the first X-ray detector to be arranged in large part (e.g., completely) inside a radiation cone of the X-ray radiation of the first radiation source, and a matrix of detector cells of the second X-ray detector is arranged completely outside the radiation cone of the X-ray radiation of the first radiation source. The respective matrix includes, for example, all the detector cells of the respective X-ray detector. The radiation cone may be predetermined between the first radiation source and the first X-ray detector by the collimator.

This has the advantage that only the scattered radiation is detected by the second X-ray detector and the X-ray radiation is acquired in a particularly large region by the first X-ray detector so that a reconstructed image accordingly has a particularly high level of quality. The advantages are therefore achieved well and securely.

An embodiment provides for the medical apparatus to include or have a biplane C-Arm system that includes the first radiation source with the assigned first X-ray detector, and a second radiation source, to which the second X-ray detector is assigned. For example, the second radiation source may be inactive or deactivated during the method.

In the case of 3D imaging, for example, in which typically only one radiation source with one X-ray detector is used, the second X-ray detector that is present in the case of the apparatuses may be used to raise the image quality and carry out scattered radiation compensation. Even in the case of 2D imaging, both radiation sources are frequently not utilized in a biplane C-arm system so that the advantages of the improved image quality already described may be achieved simply without additional hardware cost.

Another embodiment provides for the two X-ray detectors to be arranged so as to be capable of rotating around a common rotational axis, and a respective normal to the respective main plane of extension of the respective X-ray detector, which, for example, runs centrally through the matrix of detector cells, runs through the rotational axis. The X-ray detectors are therefore arranged with corresponding main planes of extension respectively tangential to a cylinder around the rotational axis. The two X-ray detectors are arranged adjacent to each other in an axial direction parallel to the rotational axis (e.g., next to each other along the patient axis) and/or arranged adjacent to each other in an azimuthal direction (e.g., a tangential direction perpendicular to the rotational axis; next to each other on a circular orbit around the rotational axis). The tangential direction perpendicular to the rotational axis may therefore be a direction that runs tangentially to a circle that stands perpendicular to the rotational axis (A). For example, the two X-ray detectors may be arranged to border on each other in this regard. For example, the X-ray detectors or a casing of the X-ray detectors may respectively abut each other or be spaced less than 10 or 5 centimeters from each other.

This has the advantage that the two X-ray detectors may be arranged in different relationships with respect to each other. Thus, in the case of arrangement parallel to the rotational axis, the estimation of the spatial distribution of the scattered radiation distribution for the first X-ray detector, the estimation being effected based on the scattered radiation acquired by the second X-ray detector, is mathematically simpler since the two main planes of extension of the X-ray detectors may run parallel to each other. In the case of arrangement in the direction perpendicular to the rotational axis, more scattered radiation may be detected by the second X-ray detector at least partly due to a scattered ray grid potentially arranged at the second X-ray detector. As a result, the statistics become better, and accordingly, the estimation of the spatial distribution of the scattered radiation for the first X-ray detector likewise becomes better. Since the X-ray detectors are respectively arranged so as to be capable of rotating, the method is also suitable for 3D imaging. The relative geometrical position and orientation of the two X-ray detectors with respect to each other are known.

In one embodiment, during the first acquisition and the second acquisition, the two X-ray detectors are rotated around the rotational axis (e.g., by more than 180 degrees). The first acquisition and the second acquisitions, for example, may be effected, for example, for a reconstruction of a 3D image.

This has the advantage that a three-dimensional image with a high quality level may be generated.

A further embodiment provides that during the determination of the component of the transmitted primary X-ray radiation acquired by the first X-ray detector, the estimated spatial distribution of the scattered radiation component in the first X-ray detector is utilized as a boundary condition for a known scattered ray correction method. For example, the estimated spatial distribution may be utilized as a boundary condition for an iterative known scattered ray correction method. In this regard, the spatial distribution may be utilized as a boundary condition for an initialization and/or a regulation of a known scattered ray correction method.

This has the advantage that the known and already highly developed and highly optimized scattered ray correction methods may be improved since the scattered radiation may be acquired particularly well via the second X-ray detector with the large detector surface, and a corresponding scattered radiation distribution may be defined particularly precisely.

In one embodiment, a size and/or a location and/or a shape and/or a material of the irradiated object may be estimated based on the scattered radiation distribution. For example, it is thus possible to estimate whether scattered radiation is caused in the case of the object, which in the example of a head is less and in the example of an abdomen is more. A size of the object may also be derived from the quantity of the scattered radiation.

This has the advantage that the additional information obtained about size and/or location and/or shape or material of the object may be utilized for generating a qualitatively improved image. Thus, for example, the information obtained may likewise be utilized as a boundary condition for known scattered ray correction methods or as a boundary condition for other image processing steps.

In one embodiment, depending on the estimated size and/or location and/or shape of the object, a truncation correction is performed on an image of the object generated (e.g., reconstructed or recorded) based on the determined component of the transmitted primary X-ray radiation. For example, a reconstruction of the 3D image depending on the truncation correction may also be effected in the case of this embodiment of the method.

This has the advantage that the truncation artifacts otherwise customarily occurring precisely in the case of a 3D reconstruction may be reduced in the case of inserting objects that, due to size, are only irradiated or penetrated by radiation in some regions, for example. This is advantageous in the case of apparatuses with comparatively small X-ray detectors. For example, this is favorable for biplane apparatuses since these typically have less sizeable detectors than other imaging apparatuses for the sake of raised mobility of the detectors.

Another embodiment provides for the first X-ray detector to be implemented with a first scattered ray grid for reducing the acquired scattered radiation, and the estimation of the spatial distribution for the scattered radiation acquired by the first X-ray detector (e.g., the scattered radiation component acquired by the first X-ray detector) to be effected based on the scattered radiation distribution acquired by the second X-ray detector depending on a first weighting function that represents an influence of the first scattered ray grid on the first intensity distribution acquired overall by the first X-ray detector. For example, the second X-ray detector may be implemented without a scattered ray grid in this regard.

This has the advantage that the scattered radiation acquired by the first X-ray detector is reduced by the scattered ray grid and the non-linear reduction in the scattered radiation being effected by the scattered ray grid may be taken into account in detail at the first X-ray detector so that overall an improved scattered radiation compensation is achieved.

A further embodiment provides for the estimation of the spatial distribution for the scattered radiation acquired by the first X-ray detector to be effected based on the scattered radiation distribution acquired by the second X-ray detector depending on a second weighting function that is dependent on an angle between the main planes of extension of the two X-ray detectors and/or a material of the object. For example, the second X-ray detector may be implemented with a second scattered ray grid for reducing the acquired scattered radiation, and the second weighting function may also represent an influence of the second scattered ray grid on the scattered radiation distribution acquired by the second X-ray detector. In this regard, the second weighting function may be dependent, for example, on an alignment of the scattered radiation grid with the second radiation source assigned to the second X-ray detector.

This has the advantage that the image quality of the imaging apparatus may be further improved. Thus, the second weighting function not only makes it possible to take account of the precise location of the X-ray detectors with respect to each other but, for example, that bones or soft tissue parts give rise to a respectively different scattered radiation distribution and scattered radiation intensity. A scattered ray grid that, for example, is aligned or optimized with respect to the second radiation source further intensifies in this regard the dependency of the scattered radiation distribution acquired by the second X-ray detector on the relative location of the two X-ray detectors. For this reason, correspondingly taking the same into account is advantageous for the scattered ray compensation.

The present embodiments also relate to a medical imaging apparatus (e.g., an X-ray apparatus and/or a computed tomography apparatus) with a first radiation source for generating a primary X-ray radiation and for irradiating an object with the primary X-ray radiation. The medical imaging apparatus includes a first X-ray detector assigned to the first radiation source for an acquisition of a first intensity distribution of an X-ray radiation that includes a component of the primary X-ray radiation transmitted through the object and also a scattered radiation generated by a scattering of the primary X-ray radiation at the object.

The medical apparatus also has a second X-ray detector for acquisition of a scattered radiation distribution of the scattered radiation generated at the object. The medical apparatus also includes a computing facility (e.g., a computer) that is configured for estimating a spatial distribution for the component of the scattered radiation acquired by the first X-ray detector based on the scattered radiation distribution acquired by the second X-ray detector. The computer is also configured for determining the component of the transmitted primary X-ray radiation acquired by the first X-ray detector from the intensity distribution acquired overall by the first X-ray detector depending on the spatial distribution estimated for the scattered radiation on the first X-ray detector.

The first X-ray detector may have a first casing, and the second X-ray detector may have a second casing different from the first casing.

The present embodiments also relate to a medical imaging apparatus configured to carry out an embodiment of the method.

Advantages and advantageous embodiments of the medical imaging apparatus correspond to the advantages and advantageous embodiments of the method.

The features and feature combinations stated above in the description, and also the features and feature combinations stated below in the description of the figures and/or shown alone in the figures may be used not only in the respectively specified combination but also in other combinations without departing from the framework of the invention. Therefore, implementations that are not explicitly shown and explained in the figures, but emerge out of and may be generated from the explained implementations by separate feature combinations, are also to be regarded as included and disclosed Implementations and feature combinations that therefore do not have all the features of an originally formulated independent claim are also to be regarded as disclosed Implementations and combinations of features (e.g., by the implementations set forth above) that go beyond or deviate from the feature combinations set forth in the cross-references of the claims are to be regarded as disclosed.

DETAILED DESCRIPTION

Figure 1:
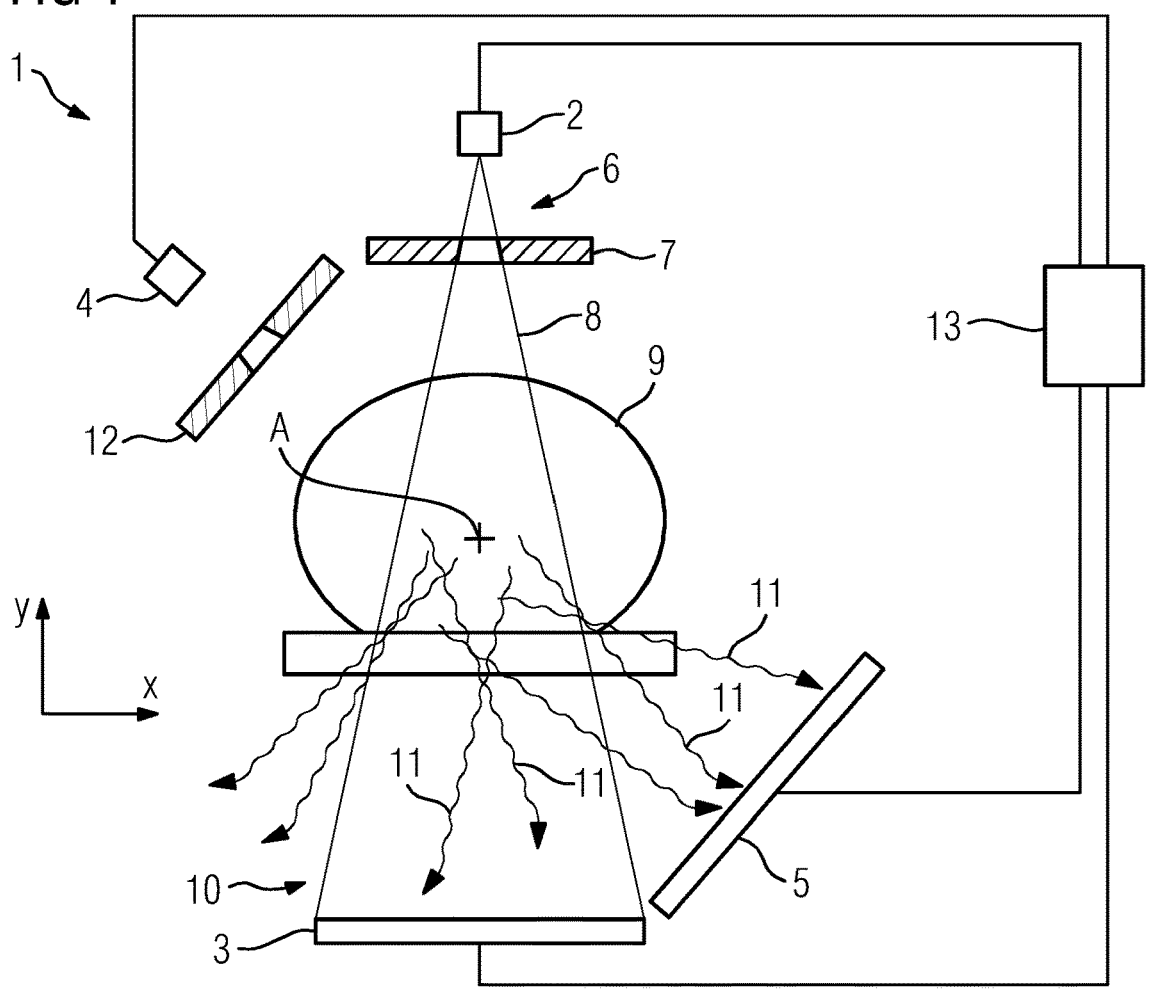
FIG. 1 shows an exemplary embodiment of a medical imaging apparatus.

FIG. 1 shows an exemplary medical imaging apparatus (e.g., a biplane C-arm system) in a cross-sectional representation. The medical apparatus 1 includes, for example, a first radiation source 2 and a first X-ray detector 3, and a second radiation source 4 with an assigned second X-ray detector 5. The first radiation source 2 generates a primary X-ray radiation 6 that is limited by, for example, a collimator 7. A further collimator 12 is arranged between the second radiation source 4 and the second X-ray detector 5. The primary radiation spreads out through the collimator 7 in a radiation cone 8. Between the radiation source 2 and the X-ray detector 3, a partial region of an object 9 is inserted in the radiation cone in this regard. The partial region of the object 9 is irradiated with the primary X-ray radiation 6. A component of the primary X-ray radiation 10 transmitted through the object 9 (e.g., a patient) is acquired by the first X-ray detector 3. A scattered radiation 11 is also generated in the object 9 by the primary X-ray radiation 6, a component of which is likewise acquired by the first X-ray detector 3. Therefore, a transmitted component of the primary X-ray radiation 10 and a component of the X-ray radiation 11 are acquired by the X-ray detector 3.

The scattered radiation 11 is also acquired proportionally by the second X-ray detector 5. The second X-ray detector 5 only acquires a further component of the scattered radiation 11 in the present case since the second radiation source 4 is deactivated during the method and the second X-ray detector 5 is arranged outside the radiation cone 8.

The two X-ray detectors 3, 5 and the assigned radiation sources 2, 4, together with the collimators 7, 12, are arranged so as to be capable of rotating around a common rotational axis A. The common rotational axis A also runs perpendicular to the drawing plane in the present case. The first radiation source or the second radiation source, respectively, and the first X-ray detector or the second X-ray detector, respectively, are arranged diametrically opposite with reference to the rotational axis A in the example shown. Accordingly, a respective normal to the respective main planes of extension of the two X-ray detectors runs through the rotational axis A.

The medical apparatus 1 also has a computing facility 13 (e.g., a computer) that, for example, is configured to estimate a spatial distribution 15 (FIG. 2) for the first intensity distribution 17 (FIG. 2) acquired by the first X-ray detector 3 based on the scattered radiation distribution 14 (FIG. 2) acquired by the second X-ray detector 5. The computer 13 is also configured to determine the component of the transmitted primary X-ray radiation 10 acquired by the first X-ray detector 3 from the intensity distribution 17 acquired overall by the first X-ray detector 3 depending on the spatial distribution 15 estimated for the scattered radiation on the first X-ray detector 3.

Figure 2:
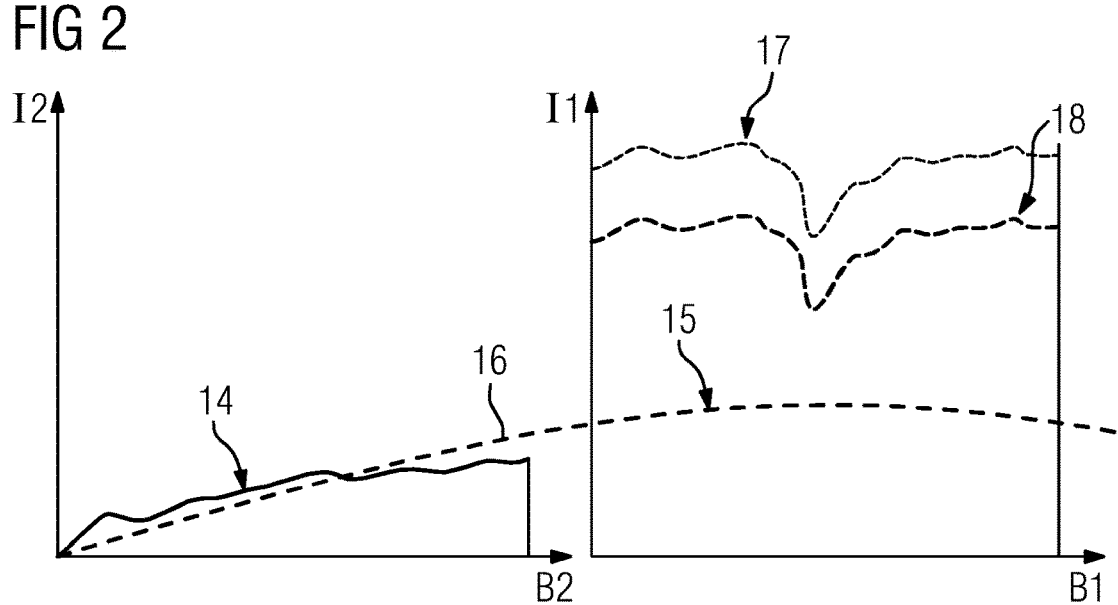
FIG. 2 shows an exemplary acquired intensity distribution of an X-ray radiation and an exemplary scattered radiation distribution with an exemplary estimated spatial distribution of the scattered radiation.

FIG. 2 represents exemplary distributions (e.g., one-dimensional distributions) for the two X-ray detectors 3, 5. Plotted respectively in this regard is the intensity I1, I2 for the X-ray radiation respectively acquired by the first X-ray detector 3 or the second X-ray detector 5, respectively (FIG. 1). The acquired intensity I2 of the second X-ray detector 5 over a width B2 of the second X-ray detector 5 is plotted on the left, and the acquired intensity I1 of the X-ray radiation acquired by the first X-ray detector 3 over a width B1 of the first X-ray detector 3 is plotted on the right. In the example shown, the corresponding main planes of extension of the X-ray detectors 3, 5 are arranged parallel with respect to each other in this regard, in contrast to the example shown in FIG. 1, for a better overview. The scattered radiation distribution 14 that is acquired by the second X-ray detector 5 is utilized to estimate a spatial distribution 15 for the scattered radiation 11 acquired by the first X-ray detector 3 with the aid of a mathematical method (e.g., quadratic). In one example, a curve 16 with a minimal quadratic deviation from the acquired scattered radiation distribution 14 is laid in this regard through the scattered radiation distribution 14 by the mathematical model. This may be extrapolated, since the first X-ray detector 3 and the second X-ray detector 5 are arranged adjacent to each other in a common coordinate model to the first detector 3 and may describe the spatial distribution 15 at that point. By stripping out this spatial distribution 15 from the intensity distribution 17 acquired overall by the first X-ray detector 3, the component of the transmitted first primary X-ray radiation 6 acquired by the first X-ray detector 3 is therefore determined in the form of a second intensity distribution 18. The scattered radiation 11 in the X-ray imaging is therefore compensated for in an efficient and precise manner.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical imaging apparatus, wherein the medical imaging apparatus comprises a biplane C-Arm system that includes a first X-ray detector assigned to a first radiation source, and a second X-ray detector assigned to a second radiation source, the method comprising:
   generating a single radiation cone of primary X-ray radiation by the first radiation source of the medical imaging apparatus;
   irradiating an object with the primary X-ray radiation;
   acquiring, in a first acquisition, an intensity distribution of an X-ray radiation by the first X-ray detector of the medical imaging apparatus, wherein the acquired intensity distribution is defined by a primary radiation component of the primary X-ray radiation transmitted through the object and a scattered radiation component of the primary X-ray radiation generated by a scattering of the primary X-ray radiation at the object;
   acquiring, in a second acquisition, a scattered radiation distribution of scattered radiation generated at the object by the second X-ray detector of the medical imaging apparatus, the scattered radiation distribution representing an intensity of acquired scattered radiation from only the single radiation cone;
   estimating a spatial distribution for the scattered radiation component of the primary X-ray radiation acquired by the first X-ray detector based on the scattered radiation distribution acquired by the second X-ray detector by a computer of the medical imaging apparatus; and
   determining an intensity distribution of the primary radiation component of the transmitted primary X-ray radiation acquired by the first X-ray detector from the intensity distribution acquired by the first X-ray detector depending on the estimated spatial distribution by the computer.

2. The method of claim 1, wherein a matrix of detector cells of the first X-ray detector is arranged at least partly inside the single radiation cone of the primary X-ray radiation, and a matrix of detector cells of the second X-ray detector is arranged completely outside the single radiation cone of the primary X-ray radiation.

3. The method of claim 2, wherein the matrix of detector cells of the first X-ray detector is arranged completely inside the single radiation cone of the primary X-ray radiation.

4. The method of claim 1, wherein the first X-ray detector and the second X-ray detector are arranged so as to be rotatable around a common rotational axis and a respective normal to a respective main plane of extension of the respective X-ray detector that runs through the common rotational axis,
wherein the first X-ray detector and the second X-ray detector are arranged adjacent to each other in a direction parallel to the common rotational axis or in a direction that runs tangentially to a circle that stands perpendicular to the rotational axis.

5. The method of claim 4, wherein during the first acquisition and the second acquisition, the first X-ray detector and the second X-ray detector are rotated around the common rotational axis.

6. The method of claim 5, wherein during the first acquisition and the second acquisition, the first X-ray detector and the second X-ray detector are rotated around the common rotational axis by more than 180°.

7. The method of claim 1, wherein during the determining of the intensity distribution of the primary radiation component of the transmitted primary X-ray radiation acquired by the first X-ray detector, the estimated spatial distribution is utilized as a boundary condition of a scattered ray correction method.

8. The method of claim 7, wherein the estimated spatial distribution is utilized as the boundary condition for an initialization, a regulation, or the initialization and the regulation of the scattered ray correction method.

9. The method of claim 7, wherein the scattered ray correction method is an iterative scattered ray correction method.

10. The method of claim 1, further comprising estimating a size, a location, a shape, a material, or any combination thereof of the irradiated object based on the scattered radiation distribution.

11. The method of claim 10, further comprising performing a truncation correction on an image of the object generated based on the determined intensity distribution of the primary radiation component of the transmitted primary X-ray radiation, depending on the estimated size, the estimated location, the estimated shape of the object, or any combination thereof.

12. The method of claim 1, wherein the first X-ray detector is implemented with a first scattered ray grid, and the estimation of the spatial distribution for the scattered radiation acquired by the first X-ray detector is effected based on the acquired scattered radiation distribution depending on a first weighting function that represents an influence of the first scattered ray grid on the intensity distribution acquired by the first X-ray detector.

13. The method of claim 1, wherein the estimation of the spatial distribution for the scattered radiation component of the primary X-ray radiation acquired by the first X-ray detector is effected based on the acquired scattered radiation distribution depending on a second weighting function that is dependent on an angle between main planes of extension of the first X-ray detector and the second X-ray detector, a material of the object, or a combination thereof.

14. The method of claim 13, wherein the second X-ray detector is implemented with a second scattered ray grid, and the second weighting function also represents an influence of the second scattered ray grid on the scattered radiation distribution acquired by the second X-ray detector.

15. The method of claim 1, wherein the first X-ray detector of the medical imaging apparatus is spaced apart from the second X-ray detector of the medical imaging apparatus, the second X-ray detector being assigned to a second radiation source.

16. A biplane C-Arm system comprising:
a first radiation source operable to:
generate a single radiation cone of primary X-ray radiation; and
irradiate an object with the primary X-ray radiation;
a first X-ray detector assigned to the first radiation source, the first X-ray detector operable to:
acquire an intensity distribution of an X-ray radiation, the intensity distribution of the X-ray radiation being defined by a primary radiation component of the primary X-ray radiation transmitted through the object and a scattered radiation component of the primary X-ray radiation generated by a scattering of the primary X-ray radiation at the object;
a second X-ray detector operable to acquire a scattered radiation distribution of scattered radiation generated at the object, the scattered radiation distribution representing an intensity of acquired scattered radiation from only the single radiation cone; and
a processor configured to:
estimate a spatial distribution for the scattered radiation component of the primary X-ray radiation acquired by the first X-ray detector based on the scattered radiation distribution acquired by the second X-ray detector; and
determine the primary radiation component of the transmitted primary X-ray radiation acquired by the first X-ray detector from the intensity distribution acquired by the first X-ray detector depending on the spatial distribution estimated for the scattered radiation on the first X-ray detector.

17. The biplane C-Arm system claim 16, wherein the first X-ray detector has a first casing, and the second X-ray detector has a second casing different from the first casing.

* * * * *

UNITED STATES PATENT AND TRADEMARK OFFICE
CERTIFICATE OF CORRECTION

| | | |
|---|---|---|
| PATENT NO. | : 11,134,904 B2 | Page 1 of 1 |
| APPLICATION NO. | : 15/803380 | |
| DATED | : October 5, 2021 | |
| INVENTOR(S) | : Günter Lauritsch et al. | |

It is certified that error appears in the above-identified patent and that said Letters Patent is hereby corrected as shown below:

In the Claims

Column 12, Line 52:
"The biplane C-Arm system claim 16, wherein the first"
Should be replaced with:
"The biplane C-Arm system of claim 16, wherein the first"

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*